United States Patent [19]
Rotstein et al.

[11] Patent Number: 5,962,531
[45] Date of Patent: Oct. 5, 1999

[54] 5-AROYLNAPHTHALENE DERIVATIVES AS ANTI-INFLAMMATORY AGENTS

[75] Inventors: David Mark Rotstein, Sunnyvale; Eric Brian Sjogren, Mountain View, both of Calif.

[73] Assignee: Syntex (U.S.A.) Inc., Palo Alto, Calif.

[21] Appl. No.: 09/013,328

[22] Filed: Jan. 26, 1998

Related U.S. Application Data

[60] Provisional application No. 60/036,466, Jan. 28, 1997.

[51] Int. Cl.$^6$ .......................... A61K 31/18; C07C 311/14
[52] U.S. Cl. ............................ 514/601; 564/102; 568/28
[58] Field of Search .............................. 564/102; 568/28; 514/601, 709

[56] References Cited

U.S. PATENT DOCUMENTS

| | | | |
|---|---|---|---|
| 3,655,679 | 4/1972 | Shen et al. | 280/295 R |
| 3,715,358 | 2/1973 | Witzel et al. | 260/263 |
| 3,755,455 | 8/1973 | Houlihan | 260/591 |
| 3,899,529 | 8/1975 | Witzel | 260/517 |
| 4,226,783 | 10/1980 | Marsh | 260/351 |
| 4,406,896 | 9/1983 | Higuchi et al. | 424/232 |
| 4,980,509 | 12/1990 | Maignan et al. | 568/28 |
| 5,484,795 | 1/1996 | Bryant et al. | 514/319 |
| 5,484,796 | 1/1996 | Bryant et al. | 514/319 |
| 5,484,797 | 1/1996 | Bryant et al. | 514/319 |
| 5,491,140 | 2/1996 | Bruns, Jr. et al. | 514/212 |

FOREIGN PATENT DOCUMENTS

| | | |
|---|---|---|
| 0 035 770 A2 | 3/1981 | European Pat. Off. . |
| 0 036 145 A1 | 3/1981 | European Pat. Off. . |
| 0 106 140 A2 | 9/1983 | European Pat. Off. . |
| 0 354 329 | 2/1990 | European Pat. Off. . |
| 0 723 956 A1 | 1/1996 | European Pat. Off. . |
| 0 729 951 A1 | 2/1996 | European Pat. Off. . |
| 0 731 093 A1 | 3/1996 | European Pat. Off. . |
| 0 733 620 A1 | 3/1996 | European Pat. Off. . |
| 384 567 | 2/1965 | Switzerland . |
| 1468111 | 1/1975 | United Kingdom . |
| WO95/01426 | 1/1995 | WIPO . |
| WO95/04530 | 2/1995 | WIPO . |
| WO96/08486 | 3/1996 | WIPO . |
| WO96/18616 | 6/1996 | WIPO . |
| WO96/18617 | 6/1996 | WIPO . |

OTHER PUBLICATIONS

Mazaleyrat, et al., *Tetrahedron Letters,* vol. 26:49, (1985), pp. 6071–6074, "Participation of a Peri–Hydroxyl Group in the Trifluoroacetolysis of Naphthalenesulfonamides".

Mustafa, *J. Chemical Society,* (1949, pp. 2151–2152, "Action of Grignard Solutions. Part III. Action of Grignard Solutions on Naphthasultone and its Substituted Derivatives".

Chemical Abstract; EN; (1960) p. 1473.

Chemical Abstract; Dziewonski, Moszew; *Rocz. Chem.,* vol. 11., (1931), pp. 169–192.

Chemical Abstract; *Chem. Zentralbl,* vol. 102; (1931) pp. 2876–2879.

Chemical Abstract; *American Chemical Society,* vol. 26, (1932) pp. 130–131.

*Primary Examiner*—Alan L. Rotman
*Assistant Examiner*—Charanjit S. Aulakh
*Attorney, Agent, or Firm*—Rohan Peries; Rekha Bansal

[57] ABSTRACT

The present invention relates to certain 5-aroylnaphthalene derivatives of formula (I):

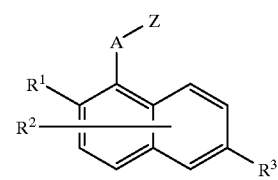

(I)

that are inhibitors of prostaglandin G/H synthase, pharmaceutical compositions containing them, methods for their use, and methods for preparing these compounds.

33 Claims, No Drawings

5-AROYLNAPHTHALENE DERIVATIVES AS ANTI-INFLAMMATORY AGENTS

CROSS-REFERENCE TO RELATED APPLICATIONS

This application claims the benefit under 35 U.S.C. 119(e) of U.S. Provisional Application Ser. No. 60/036,466 filed Jan. 28, 1997.

BACKGROUND OF THE INVENTION

1. Field of the Invention

This invention relates to anti-inflammatory and analgesic compounds, especially to certain 5-aroylnaphthalene derivatives, pharmaceutical compositions containing them, methods for their use, and methods for preparing these compounds.

2. Description of the Related Art

U.S. Pat. No. 3,899,529 (Merck) discloses aroyl substituted naphthaleneacetic acids useful as anti-inflammatory agents, anti-pyretic, and analgesic agents.

U.S. Pat. No. 3,755,455 (Sandoz) discloses (1-alkoxy-2-naphthyl)substituted or unsubstituted phenyketones useful as anti-inflammatory agents.

SUMMARY OF THE INVENTION

In a first aspect, this invention provides compounds selected from the group of compounds represented by formula (I):

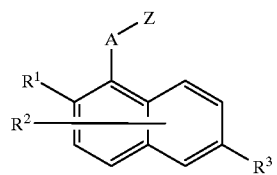

(I)

wherein:

A is a bond, —CH$_2$—, —CH(OH)—, —C=NOR$^4$—, —C(O)—, -NR$^5$—, —O—, or —S(O)$_n$— where n is an integer from 0 to 2, R$^4$ is hydrogen or alkyl, and R$^5$ is hydrogen, alkyl, or acyl;

Z is a group represented by formula (B), (C), (D), or (E):

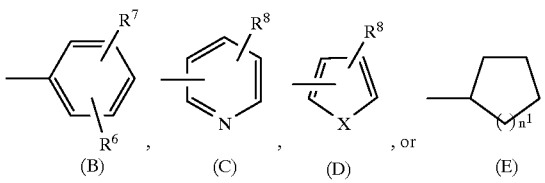

where:

n$^1$ is 0 to 3;

X is O or S;

R$^6$ and R$^7$ are independently selected from hydrogen, alkyl, haloalkyl, cycloalkyl, cycloalkylalkyl, acyl, alkylthio, cycloalkylthio, cycloalkylalkylthio, alkoxy, cycloalkyloxy, cycloalkylalkyloxy, haloalkyloxy, alkenyl, halo, cyano, nitro, hydroxy, or —NR$^9$R$^{10}$ where R$^9$ and R$^{10}$ are independently hydrogen, alkyl, or acyl; or R$^6$ and R$^7$ when they are adjacent to each other form methylenedioxy or ethylenedioxy;

R$^8$ is hydrogen, alkyl, haloalkyl, alkoxy, cycloalkyloxy, haloalkyloxy, alkylthio, cycloalkylthio, nitro, cyano, hydroxy, or halo;

R$^1$ is hydrogen, alkyl, alkenyl, alkynyl, haloalkyl, cycloalkyl, cycloalkylalkyl, alkoxy, alkenyloxy, cycloalkyloxy, cycloalkylalkyloxy, haloalkyloxy, hydroxyalkyloxy, alkoxyalkyloxy, alkylthio, cycloalkylthio, cycloalkylalkylthio, hydroxy, halo, cyano, carboxy, alkoxycarbonyl, acyl, —C=NOR$^4$, —NR$^9$R$^{10}$, —CONR$^9$R$^{10}$, —OCONR$^9$R$^{10}$, or —OSO$_2$R$^{11}$ where R$^4$, R$^9$, and R$^{10}$ are as previously defined and R$^{11}$ is alkyl, cycloalkyl, or haloalkyl;

R$^2$ is hydrogen, alkyl, alkoxy, halo, nitro, or —NR$^9$R$^{10}$; and

R$^3$ is —SO$_2$R$^{12}$ or —SO$_2$NR$^{13}$R$^{14}$ where:

R$^{12}$ is alkyl, hydroxyalkyl, alkoxyalkyl, carboxyalkyl, or alkoxycarbonylalkyl;

R$^{13}$ is hydrogen, alkyl, or acyl; and

R$^{14}$ is hydrogen, alkyl, haloalkyl, cycloalkyl, cycloalkylalkyl, alkenyl, hydroxyalkyl, alkoxyalkyl, alkoxycarbonylalkyl, amino, aminoalkyl, aryl, aralkyl, heteroaralky, heterocyclo, heterocycloalkyl, acyl, hydroxy, or alkoxy; or R$^{13}$ and R$^{14}$ together with the nitrogen atom to which they are attached form a heterocycloamino group; and their pharmaceutically acceptable salts, prodrugs, individual isomers, and mixtures of isomers.

In a second aspect, this invention provides pharmaceutical compositions containing a therapeutically effective amount of a compound of formula (I) or its pharmaceutically acceptable salt and a pharmaceutically acceptable excipient.

In a third aspect, this invention provides a method of treatment of a disease, in particular inflammatory and autoimmune diseases, in a mammal treatable by administration of a prostaglandin G/H synthase inhibitor, comprising administration of a therapeutically effective amount of a compound of formula (I) or its pharmaceutically acceptable salt.

In a fourth aspect, this invention provides processes for preparing compounds of formula (I).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkenyl" means a linear monovalent hydrocarbon radical of two to six carbon atoms or a branched monovalent hydrocarbon radical of three to six carbon atoms containing at least one double bond, e.g., ethenyl, 2-propenyl, and the like.

"Alkynyl" means a linear monovalent hydrocarbon radical of two to six carbon atoms or a branched monovalent hydrocarbon radical of three to six carbon atoms containing at least one triple bond, e.g., ethynyl, propynyl, butynyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Cycloalkyl" means a cyclic saturated monovalent hydrocarbon radical of three to seven carbon atoms, e.g., cyclopropyl, cyclohexyl, and the like.

"Halo" means fluoro, chloro, bromo, and iodo.

"Haloalkyl" means alkyl substituted with one or more halogen atoms, preferably one to three halogen atoms, preferably fluorine or chlorine, including those substituted with different halogens, e.g., $-CH_2Cl$, $-CF_3$, $-CH_2CF_3$, $-CF_2CF_3$, $-CH_2CCl_3$, and the like.

"Alkoxy", "alkenyloxy", "cycloalkyloxy", or "haloalkyloxy" means a radical —OR where R is alkyl, alkenyl, cycloalkyl, or haloalkyl respectively as defined above, e.g., methoxy, ethoxy, propoxy, 2-propoxy, ethenyloxy, cyclopropyloxy, cyclobutyloxy, $-OCH_2Cl$, $-OCF_3$, and the like.

"Alkylthio" or "cycloalkylthio" means a radical —SR where R is alkyl or cycloalkyl respectively as defined above, e.g., methylthio, butylthio, cyclopropylthio, and the like.

"Acyl" means a radical —C(O)R where R is hydrogen, alkyl, or haloalkyl as defined above, e.g., formyl, acetyl, trifluoroacetyl, butanoyl, and the like.

"Amino" means a radical —$NH_2$

"Monosubstituted amino" means a radical —NHR where R is alkyl or acyl, e.g., methylamino, (1-methylethyl)amino, and the like.

"Disubstituted amino" means a radical —NRR' where R and R' are independently alkyl or acyl, e.g., dimethylamino, methylethylamino, di(1-methylethyl)amino, and the like.

"Hydroxyalkyl" means a linear monovalent hydrocarbon radical of two to six carbon atoms or a branched monovalent hydrocarbon radical of three to six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4hydroxybutyl, 2,3-dihydroxypropyl, 1-(hydroxymethyl)-2-hydroxyethyl, 2,3-dihydroxybutyl, 3,4dihydroxybutyl and 2-(hydroxymethyl)-3-hydroxypropyl, preferably 2-hydroxyethyl, 2,3dihydroxypropyl, and 1-(hydroxymethyl)-2-hydroxyethyl.

"Alkoxyalkyl" means a linear monovalent hydrocarbon radical of one to six carbon atoms or a branched monovalent hydrocarbon radical of three to six carbons substituted with at least one alkoxy group as defined above, e.g., 2-methoxyethyl, 2-methoxypropyl, and the like.

"Hydroxyalkyloxy" or "alkoxyalkyloxy" means a radical- OR where R is hydroxyalkyl or alkoxyalkyl respectively as defined above, e.g., 2-hydroxyethyloxy, 2-methoxyethyloxy, and the like.

"Aminoalkyl" means a linear monovalent hydrocarbon radical of two to six carbon atoms or a branched monovalent hydrocarbon radical of three to six carbons substituted with at least one —NRR' where R and R' are independently selected from hydrogen, alkyl, or acyl, e.g., 2-aminoethyl, 2-N,N-diethylaminopropyl, 2-N-acetylaminoethyl, and the like.

"Aryl" means a monovalent monocyclic or bicyclic aromatic hydrocarbon radical of 6 to 12 ring atoms, and optionally substituted independently with one or more substituents, preferably one or two substituents, selected from alkyl, haloalkyl, cycloalkyl, alkoxy, alkylthio, halo, nitro, acyl, cyano, amino, monosubstituted amino, disubstituted amino, -hydroxy, carboxy, or alkoxycarbonyl. Representative examples include, but are not limited to, phenyl, biphenyl, 1-naphthyl, and 2-naphthyl and the derivatives thereof.

"Heteroaryl" means a monovalent monocyclic or bicyclic aromatic radical of 5 to 10 ring atoms containing one or more, preferably one or two ring heteroatoms selected from N, O, or S, the remaining ring atoms being C. The heteroaryl ring is optionally substituted independently with one or more substituents, preferably one or two substituents, selected from alkyl, haloalkyl, cycloalkyl, alkoxy, alkylthio, halo, nitro, acyl, cyano, amino, monosubstituted amino, disubstituted amino, hydroxy, carboxy, or alkoxycarbonyl. More specifically the term heteroaryl includes, but is not limited to, pyridyl, pyrrolyl, thienyl, furanyl, indolyl, quinolyl, benzopyranyl, and thiazolyl, and the derivatives thereof.

"Heterocycloamino" means a saturated monovalent cyclic group of 3 to 8 ring atoms, wherein at least one ring atom is N and optionally contains a second ring heteroatom selected from the group consisting of N, O, or $S(O)_n$ (where n is an integer from 0 to 2), the remaining ring atoms being C. The heterocycloamino ring may be optionally fused to a benzene ring or it may be optionally substituted independently with one or more substituents, preferably one or two substituents, selected from alkyl, haloalkyl, cycloalkyl, cycloalkylalkyl, aryl, aralkyl, heteroaryl, heteroaralkyl, halo, cyano, acyl, amino, monosubstituted amino, disubstituted amino, carboxy, or alkoxycarbonyl. More specifically the term heterocycloamino includes, but is not limited to, pyrrolidino, piperidino, morpholino, piperazino, indolino, and thiomorpholino, and the derivatives thereof.

"Heterocyclo" means a saturated monovalent cyclic group of 3 to 8 ring atoms in which one or two ring atoms are heteroatoms selected from N, O, or $S(O)_n$, where n is an integer from 0 to 2, the remaining ring atoms being C. The heterocyclo ring may be optionally fused to a benzene ring or it may be optionally substituted independently with one or more substituents, preferably one or two substituents, selected from alkyl, haloalkyl, cycloalkyl, cycloalkylalkyl, aryl, aralkyl, heteroaralkyl, halo, cyano, acyl, monosubstituted amino, disubstituted amino, carboxy, or alkoxycarbonyl. More specifically the term heterocyclo includes, but is not limited to, pyrrolidino, piperidino, morpholino, piperazino, tetrahydropyranyl, and thiomorpholino, and the derivatives thereof.

"Cycloalkylalkyl" means a radical -$R^a R^b$ where $R^a$ is an alkylene group and $R^b$ is a cycloalkyl group as defined above e.g., cyclopropylmethyl, cyclohexylpropyl, 3-cyclohexyl-2-methylpropyl, and the like.

"Cycloalkylalkyloxy" means a radical —OR where R is a cycloalkylalkyl group as defined above e.g., cyclopropylmethyloxy, 3-cyclohexylpropyloxy, and the like.

"Aralkyl" means a radical -$R^a R^b$ where $R^a$ is an alkylene group and $R^b$ is an aryl group as defined above e.g., benzyl, phenylethyl, 3-(3-chlorophenyl)-2-methylpentyl, and the like.

"Heteroaralkyl" means a radical -$R^a R^b$ where $R^a$ is an alkylene group and $R^b$ is a heteroaryl group as defined above e.g., 2-,3-, or 4-pyridylmethyl, furan-2-ylmethyl and the like.

"Heterocycloalkyl" means a radical -$R^a R^b$ where $R^a$ is an alkylene group and $R^b$ is a heterocyclo group as defined above e.g., morpholin-4-ylethyl, tetrahydrofuran-2-ylmethyl and the like.

"Pro-drugs" means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

"Optional" or "optionally" means that the subsequently described event or circumstance may but need not occur, and that the description includes instances where the event or circumstance occurs and instances in which it does not. For example, "heterocyclo group optionally mono- or di- substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (–)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)- stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxyl-amino, and the like.

Nomenclature

The naming and numbering of the compounds of this invention is illustrated below. The naphthalene nucleus of the compounds of formula (I) are numbered as follows:

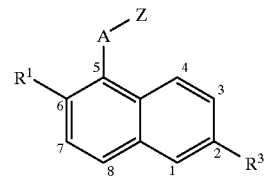

Side chains of the Z substituent are numbered as shown below:

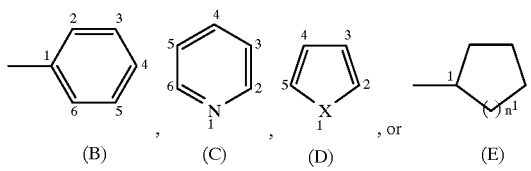

(B)    (C)    (D)    , or    (E)

The pyridine, thiophene, and furan rings can be linked to A at any position on the ring other than 1-position.

Accordingly, the pyridine ring can be 2-, 3-, or 4-pyridyl, the thiophene ring can be 2- or 3-thienyl, and the furan ring can be 2- or 3-furyl.

The nomenclature used in this application is generally based on the IUPAC recommendations.

Representative compounds of this invention are as follows

I. Compounds of formula (I) where A is —C(O)—, Z=group represented by formula (B), $R^2$=hydrogen, and $R^3$ is at the 2-position wherein $R^3$=—$SO_2NR^{13}R^{14}$ and the other groups are as defined below are:

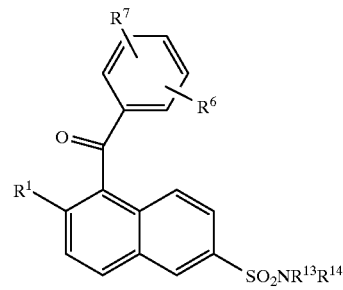

| CPD # | $R^1$ | $R^6$ | $R^7$ | $R^{13}$ | $R^{14}$ | M. Pt. °C. | Mass. Spec. m/e |
|---|---|---|---|---|---|---|---|
| 1 | OMe | H | 4-F | H | H | 172.2–172.8 | |
| 2 | OH | H | 4-F | H | H | 166.5–166.9 | |
| 3 | OMe | H | 4-F | H | acetyl | foam | 401 |
| 4 | OMe | H | 4-Me | H | H | 203–203.5 | |
| 5 | $OC_2H_5$ | H | 4-F | H | H | 138.8–139.7 | |
| 6 | OMe | H | 4-Cl | H | H | 188.1–188.7 | |
| 7 | OMe | H | 4-F | H | $n\text{-}C_4H_9$ | | 415 |
| 8 | OMe | H | 4-F | H | 2-methoxyethyl | | 417 |
| 9 | OMe | H | 4-F | H | 2-propyl | | 401 |
| 10 | OMe | H | 4-F | H | 2-hydroxyethyl | | 403 |
| 11 | OMe | H | 4-F | H | t-butyl | | 415 |
| 12 | OMe | H | 4-F | Me | Me | | 387 |
| 13 | OMe | H | 3-Cl | H | H | | 315 |
| 14 | OMe | H | 2-F | H | H | | 359 |
| 15 | OMe | H | 3-F | H | H | | 359 |
| 16 | OMe | H | 2-Me | H | H | | 355 |
| 17 | OMe | H | 2-Br | H | H | | 419 |
| 18 | OMe | H | 3-Br | H | H | | 419 |
| 19 | OMe | 2-Cl | 4-Cl | H | H | | 409 |
| 20 | OMe | 2-F | 4-F | H | H | | 377 |
| 21 | OMe | 2-Cl | 4-F | H | H | | 393 |
| 22 | OMe | H | 4-F | H | Me | | 373 |
| 23 | OMe | H | H | H | H | 151.5–151.9 | |
| 24 | OMe | H | 4-F | H | benzyl | | 449 |
| 25 | OMe | H | 4-F | H | ethyl | | 387 |
| 26 | OMe | H | 4-F | H | 2-phenylethyl | | 463 |
| 27 | OMe | H | 4-F | n-pentyl | n-pentyl | | 499 |
| 28 | OMe | H | 4-F | H | n-propyl | | 401 |
| 29 | OMe | H | 4-F | H | 3-hydroxypropyl | | 417 |
| 30 | OMe | H | 4-F | H | 2-(morpholin-4-yl)ethyl | | 472 |
| 31 | OMe | H | 4-F | H | 3-(morpholin-4-yl)propyl | | 486 |
| 32 | OMe | H | 4-F | H | pyridin-2-ylmethyl | | 450 |
| 33 | OMe | H | 4-F | H | pyridin-4-ylmethyl | | 450 |
| 34 | OMe | H | 4-F | H | 2-(pyridin-4-yl)ethyl | | 464 |
| 35 | OMe | H | 4-F | H | 1-(RS)-(hydroxymethyl)ethyl | | 417 |
| 36 | OMe | H | 4-F | ethyl | ethyl | | 415 |
| 37 | OMe | H | 4-F | H | furan-2-ylmethyl | | 439 |
| 38 | OMe | H | 4-F | H | cyclopropyl | | 399 |
| 39 | OMe | H | 4-F | H | cyclohexyl | | 441 |
| 40 | OMe | H | 2-Cl | H | H | | 375 |
| 41 | OMe | 2-F | 4-$CF_3$ | H | H | | 427 |
| 42 | OMe | 2-$CF_3$ | 4-F | H | H | | 427 |
| 43 | OMe | 2-Cl | 6-Cl | H | H | | 409 |
| 44 | OMe | H | 4-$CF_3$ | H | H | | 409 |
| 45 | OMe | H | 3-Me | H | H | | 355 |
| 46 | OMe | H | 4-1-butyl | H | H | | 397 |
| 47 | OMe | 2-F | 4-Cl | H | H | | 393 |

-continued

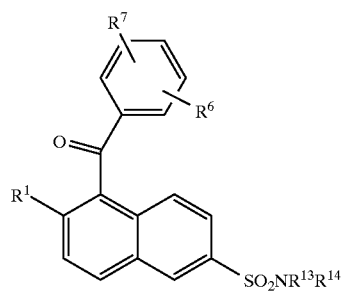

| CPD # | $R^1$ | $R^6$ | $R^7$ | $R^{13}$ | $R^{14}$ | M. Pt. °C. | Mass. Spec. m/e |
|---|---|---|---|---|---|---|---|
| 48 | OMe | 2-Cl | 4-Br | H | H | | 453 |
| 49 | OMe | 3-Cl | 4-Cl | H | H | | 409 |
| 50 | OMe | H | 4-Br | H | H | | 419 |
| 51 | OMe | H | 4-MeS | H | H | | 387 |
| 52 | OMe | 2-F | 6-F | H | H | | 377 |
| 53 | OMe | H | 4-F | H | 4-(N,N-diethylamino)-1-(RS)-methylbutyl | | 500 |
| 54 | OMe | H | 4-F | H | 1-(RS)-(hydroxymethyl)-2-methylpropyl | | 445 |
| 55 | OMe | H | 4-F | H | 1-(S)-phenylethyl | | 463 |
| 56 | OMe | H | 4-F | H | 1-(R)-phenylethyl | | 463 |
| 57 | OMe | H | 4-F | H | methoxycarbonylmethyl | | 431 |
| 58 | OMe | H | 4-F | H | 2-methyl-2-propenyl | | 413 |
| 59 | OMe | H | 4-F | H | 1-benzylpiperidin-4-yl | | 532 |
| 60 | OMe | H | 4-F | Me | 1-(1,4-benzodioxan-2-yl-methyl)piperidin-4-yl | | 604 |
| 61 | OMe | 3-Cl | 5-Cl | H | H | | 409 |
| 62 | OMe | H | 4-OH | H | H | 225–225.6 | |
| 63 | H | H | 4-F | H | H | 189.9–190.5 | |
| 64 | CN | H | 4-F | H | H | 192.1–192.9 | |
| 65 | Me | H | 4-F | H | H | 175.5–177 | |
| 66 | Cl | H | 4-F | H | H | 229.6–229.8 | |
| 67 | CN | H | 2-F | H | H | | 354 |
| 68 | $OSO_2CF_3$ | H | 4-F | H | H | | 478 |
| 69 | $C(O)NH_2$ | H | 4-F | H | H | | 372 |
| 70 | $OSO_2Me$ | H | 4-F | H | H | | 423 |
| 71 | OH | H | 2-F | H | H | 194.4–195.7 | |
| 72 | OMe | H | $3-NO_2$ | H | H | 213.5–214 | |
| 73 | CN | 2-F | 4-F | H | H | | |
| 74 | $OCONMe_2$ | H | 4-F | H | H | 202.6–203.1 | |
| 75 | OMe | H | $3-NH_2$ | H | H .HCl | 238.9–240.3 | |
| 76 | OMe | H | 4-MeO | H | H | 173.7–174.1 | |
| 77 | OMe | H | $4-NO_2$ | H | H | 225.2–225.9 | |
| 78 | 2-hydroxy-ethoxy | H | 4-F | H | H | Foam | |
| 79 | COOH | H | 4-MeO | H | H | | 385 |
| 80 | OH | 2-F | 6-F | H | H | | 363 |
| 81 | COOH | H | 4-OH | H | H | | 371 |
| 82 | OMe | H | $4-NH_2$ | H | H | 277.3–277.7 | |
| 83 | OMe | H | 4-F | H | 3-(pyrrolidin-2-one)propyl | | 484 | and are named as:

1. 5-(4-fluorobenzoyl)-6-methoxy-2-naphthalenesulfonamide.

4. 5-(4-methylbenzoyl)-6-methoxy-2-naphthalenesulfonamide.

10. N-(2-hydroxyethyl)-5-(4-fluorobenzoyl)-6-methoxy-2-naphthalenesulfonamide.

14. 5-(2-fluorobenzoyl)-6-methoxy-2-naphthalenesulfonamide.

15. 5-(3-fluorobenzoyl)-6-methoxy-2-naphthalenesulfonamide.

30. N-[2-(morpholin-4-yl)ethyl]-5-(4-fluorobenzoyl)-6-methoxy-2-naphthalenesulfonamide.

41. 5-(2-fluoro-4-trifluoromethylbenzoyl)-6-methoxy-2-naphthalenesulfonamide.

51. 5-(4-methylthioxenzoyl)-6-methoxy-2-naphthalenesulfonamide.

64. 5-(4-fluorobenzoyl)-6-cyano-2-naphthalenesulfonamide.

79. 5-(4-methoxybenzoyl)-6-carboxy-2-naphthalenesulfonamide.

II. Compounds of formula I where A is —C(O)—, Z=group represented by formula (B), $R^2$=hydrogen, and $R^3$ is at the 2-position wherein $R^3$=—$SO_2NR^{13}R^{14}$ and the other groups are as defined below are:

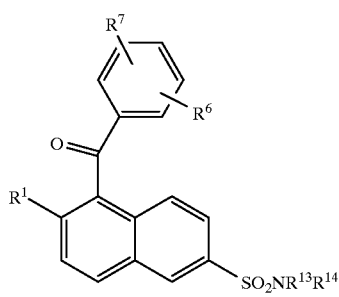

| CPD # | R¹ | R⁶ | R⁷ | NR¹³R¹⁴ | Mass. Spec. m/e |
|---|---|---|---|---|---|
| 84 | OMe | H | 4-F | 4-methylpiperazino | 442 |
| 85 | OMe | H | 4-F | 4-phenylpiperazino | 504 |
| 86 | OMe | H | 4-F | pyrrolidino | 413 |
| 87 | OMe | H | 4-F | morpholino | 429 |
| 88 | OMe | H | 4-F | piperidino | 427 |
| 89 | OMe | H | 4-F | 4-(4-fluorophenyl)piperazino | 522 |
| 90 | OMe | H | 4-F | 2(R),6(S)-dimethylmorpholino | 457 | and are named as:

84. 5-(4-fluorobenzoyl)-6-methoxy-2-(4-methylpiperazin-1-ylsulfonyl)naphthalene.

88. 5-(4-flurobenzoyl)-6-methoxy-2-(piperidin-1-ylsulfonyl)naphthalene.

III. Compounds of formula I where A is —C(O)—, Z=group represented by formula (B), R²=hydrogen, and R³=—SO₂R¹² is at the 2-position and the other groups are as defined below are:

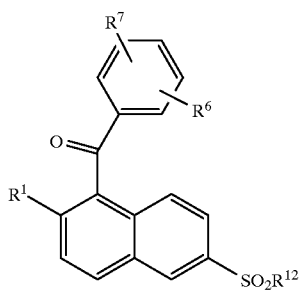

| CPD # | R¹ | R⁶ | R⁷ | R¹² | M. Pt. °C. | Mass. Spec. m/e |
|---|---|---|---|---|---|---|
| 91 | OMe | H | 4-F | Me | foam | 358 |

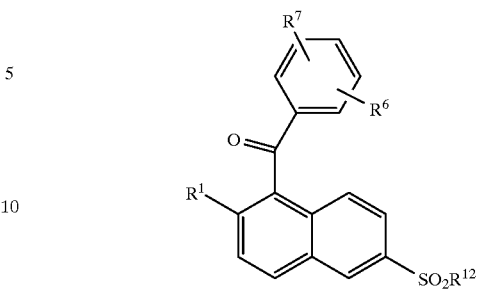

| CPD # | R¹ | R⁶ | R⁷ | R¹² | M. Pt. °C. | Mass. Spec. m/e |
|---|---|---|---|---|---|---|
| 92 | OH | H | 4-F | Me | 174.9–176 | |
| 93 | OH | H | H | Me | oil | 326 |
| 94 | OMe | H | H | Me | oil | 340 |
| 95 | H | H | 4-F | Me | 162–163 | |
| 96 | CN | H | 4-F | Me | 173.5–174.1 | |
| 97 | CN | H | H | Me | 181.5–182 | |
| 98 | Cl | H | H | Me | 133.1–133.4 | |
| 99 | CN | H | 2-F | Me | 159.7–160.2 | |
| 100 | Cl | H | 4-Cl | Me | 168.8–169.8 | |
| 101 | Me | H | 2-F | Me | 131.5–131.8 | |
| 102 | H | H | H | Me | 82–86.5 | |
| 103 | OMe | H | 4-Me | Me | 88.4–123.4 | |
| 104 | CN | H | 4-Cl | Me | 183.5–184.4 | |
| 105 | CN | H | 4-Me | Me | 183.7–184.1 | |
| 106 | OCH₂CONMe₂ | H | 4-F | Me | | 429 |
| 107 | O(CH₂)₂OH | H | 4-F | Me | | 381 |
| 108 | CONH₂ | H | H | Me | 223.4–224.3 | |
| 109 | CONH₂ | H | 4-F | Me | 223.4–224.3 | | and are named as:

91. 5-(4-fluorobenzoyl)-6-methoxy-2-methylsulfonylnaphthalene.

92. 5-(4-fluorobenzoyl)-6-hydroxy-2-methylsulfonylnaphthalene.

93. 5-benzoyl-6-hydroxy-2-methylsulfonylnaphthalene.

94. 5-benzoyl-6-methoxy-2-methylsulfonylnaphthalene.

95. 5-(4-fluorobenzoyl)-6-cyano-2-methylsulfonylnaphthalene.

97. 5-benzoyl-6-cyano-2-methylsulfonylnaphthalene.

99. 5-(2-fluorobenzoyl)-6-cyano-2-methylsulfonylnaphthalene.

104. 5-(4-chlorobenzoyl)-6-cyano-2-methylsulfonylnaphthalene.

107. 5-(4-fluorobenzoyl)-6-hydroxyethyloxy-2-methylsulfonylnaphthalene.

IV. Miscellaneous compounds

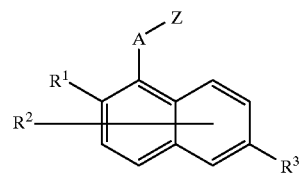

| CPD # | A | Z | R¹ | R² | R³ | M. Pt. °C. | Mass Spec. m/e |
|---|---|---|---|---|---|---|---|
| 110 | —CH₂— | 4-fluorophenyl | OMe | H | —SO₂NH₂ | 165.1–167 | |
| 111 | —C(O)— | thiophen-2-yl | OMe | H | —SO₂NH₂ | | 347 |

-continued

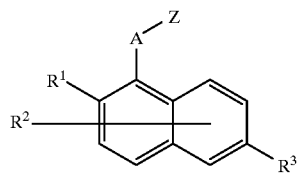

| CPD # | A | Z | $R^1$ | $R^2$ | $R^3$ | M. Pt. °C. | Mass Spec. m/e |
|---|---|---|---|---|---|---|---|
| 112 | —C(O)— | furan-3-yl | OMe | H | —SO$_2$NH$_2$ | | 33.1 |
| 113 | —SO$_2$— | 4-fluorophenyl | OMe | H | —SO$_2$Me | 205.9–206.2 | | and are named as:

110. 5-(4-fluorobenzyl)-6-methoxy-2-naphthalenesulfonamide 113. 5-(4-fluorophenylsulfonyl)-6-methoxy-2-methylsulfonylnaphthalene.

PREFERRED EMBODIMENTS

While the broadest definition of this invention is set forth in the Summary of the Invention, certain compounds of formula (I) are preferred. For example, (i) One preferred group of compounds is that wherein:
A is —C(O)—.

(ii) A second preferred group of compounds is that wherein:
A is —C=NOR$^4$— where R$^4$ is hydrogen or alkyl.

(iii) A third preferred group of compounds is that wherein:
A is —O—, —S—, or —NR$^5$— where R$^5$ is hydrogen, alkyl, or acyl.

Within these preferred groups a more preferred group of compounds is that wherein:

Z is represented by formula (B) where R$^6$ and R$^7$ are independently selected from hydrogen, alkyl, cycloalkyl, alkoxy, ethenyl, halo, or —NR$^9$R$^{10}$ (where R$^9$ and R$^{10}$ are alkyl, preferably methyl), preferably hydrogen, alkyl, alkoxy, or halo, most preferably hydrogen, methyl, methoxy, fluoro, or chloro; and R$^2$ is hydrogen.

Another more preferred group of compounds is that wherein:

Z is represented by formula (D) where X is S and R$^8$ is hydrogen; and

R$^2$ is hydrogen.

Within these preferred and more preferred groups a particularly preferred group of compounds is that wherein:

R$^1$ is preferably hydrogen, alkyl, alkoxy, cycloalkyloxy, hydroxyalkyloxy, hydroxy, halo or cyano, more preferably hydrogen, methyl, methoxy, cyclopropyloxy, 2-hydroxyethyloxy, hydroxy, chloro, or cyano, most preferably hydrogen, methyl, methoxy, hydroxy, chloro, or cyano; and R$^3$ is —SO$_2$R$^{12}$ where R$^{12}$ is alkyl, preferably methyl.

Another particularly preferred group of compounds is that wherein:

R$^1$ is preferably hydrogen, alkyl, alkoxy, cycloalkyloxy, hydroxyalkyloxy, hydroxy, halo or cyano, more preferably hydrogen, methyl, methoxy, cyclopropyloxy, 2-hydroxyethyloxy, hydroxy, chloro, or cyano, most preferably hydrogen, methyl, methoxy, hydroxy, chloro, or cyano; and R$^3$ is —SO$_2$NR$^{13}$R$^{14}$ where R$^{13}$ is hydrogen and R$^{14}$ is hydrogen, methyl, 2-hydroxyethyl, or hydroxy, more preferably R$^{14}$ is hydrogen.

Exemplary particularly preferred compounds are
5-(4-fluorobenzoyl)-6-methoxy-2-naphthalenesulfonamide.
5-(4-methylbenzoyl)-6-methoxy-2-naphthalenesulfonamide.
5-(2-fluorobenzoyl)-6-methoxy-2-naphthalenesulfonamide.
5-(3-fluorobenzoyl)-6-methoxy-2-naphthalenesulfonamide.
5-(4-fluorobenzoyl)-6-methoxy-2-methylsulfonylnaphthalene.
5-(4-fluorobenzoyl)-6-hydroxy-2-methylsulfonylnaphthalene.
5-benzoyl-6-hydroxy-2-methylsulfonylnaphthalene.
5-benzoyl-6-methoxy-2-methylsulfonylnaphthalene.
5-benzoyl-6-cyano-2-napthalenesulfonamide.
5-(4-fluorobenzoyl)-6-cyano-2-naphthalenesulfonamide.
5-(4-fluorobenzoyl)-6-methyl-2-naphthalenesulfonamide.
5-(4-fluorobenzoyl)-6-chloro-2-naphthalenesulfonamide.
5-(2-fluorobenzoyl)-6-cyano-2-naphthalenesulfonamide.
5-(2-fluorobenzoyl)-6-hydroxy-2-naphthalenesulfonamide.
5-(2-fluorobenzoyl)-6-chloro-2-naphthalenesulfonamide.
5-(2-fluorobenzoyl)-6-methyl-2-naphthalenesulfonamide.
5-(4-methylbenzoyl)-6-cyano-2-naphthalenesulfonamide.
5-(4-fluorobenzoyl)-6-cyano-2-methylsulfonylnaphthalene.
5-benzoyl- 6-cyano-2-methylsulfonylnaphthalene .
5-(4-chlorobenzoyl)-6-cyano-2-methylsulfonylnaphthalene.
5-(2-fluorobenzoyl)-6-cyano-2-methylsulfonylnaphthalene.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989); *Organic Reactions*, Volumes 1–40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Preparation of Compounds of Formula I

Scheme A describes the synthesis of a compound of formula (1) where A is —C(O)— and $R^3$ is —$SO_2R^{12}$ or —$SO_2NR^{13}R^{14}$ from a naphthalene of formula 1 where $R^1$ is an ortho-para directing group.

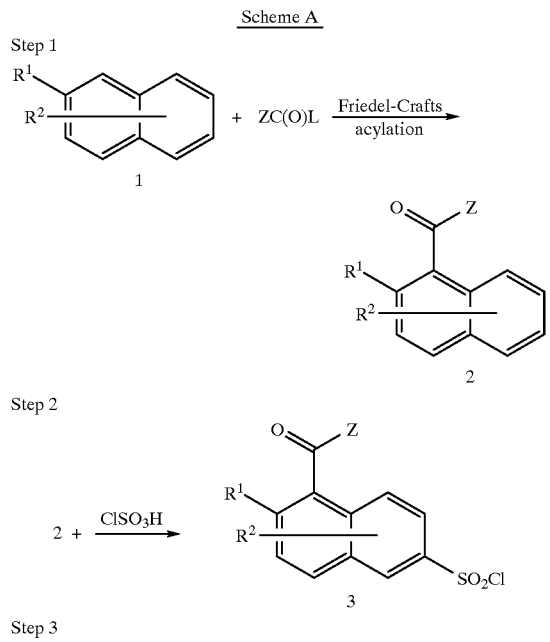

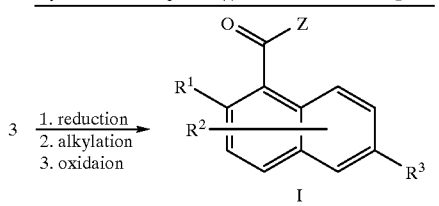

Method B:
Synthesis of compound (I) where $R^3$ is ——$SO_2NR^{13}R^{14}$

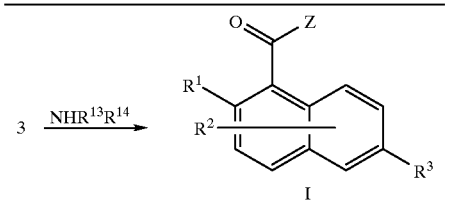

In step 1, a 5-aroylnaphthalene of formula 2 is prepared by acylating a naphthalene of formula 1, with an acylating agent ZC(O)L, where Z is as defined in the Summary of the Invention and L is a leaving group under Friedel-Crafts acylating conditions (e.g., halo, preferably chloro). The reaction is carried out in the presence of a Lewis acid such as aluminum chloride, tin chloride, and the like. Suitable solvents for the reaction are halogenated hydrocarbons such as dichloromethane, dichloroethane, and the like. In general, the compounds of formula 1 and the acid halides are commercially available or can readily be synthesized by those of ordinary skill in the art.

In step 2, a 5-aroylnaphthalene-2-sulfonyl chloride of formula 3 is prepared by reacting the compound of formula 2 with chlorosulfonic acid. The sulfonylation reaction can be carried out either in neat chlorosulfonic acid or in halogenated hydrocarbons such as dichloromethane and the like.

In step 3, a compound of formula (I) where $R^3$ is —$SO_2R^{12}$ or —$SO_2NR^{13}R^{14}$ is prepared from the 5-aroylnaphthalene-2-sulfonyl chloride 3 by following method A or method B respectively, as described below.

In method A, compound (I) where $R^3$ is —$SO_2R^{12}$ is prepared by carrying out reduction, alkylation, and oxidation steps on compound 3. The reduction of the sulfonyl chloride group to the thiol is carried out in the presence of triphenylphosphine by following the procedure described in Oae, S. and Togo, H., Bull. Chem. Soc. Jpn., 56, 3802, (1983). The thiol is alkylated to give the thioether by reacting it with an alkylating agent $R^{12}L$ where $R^{12}$ is as defined in the Summary of the Invention and L is a leaving group under alkylating conditions, (e.g.; halo, methanesulfonate, p-toluenesulfonate, and the like). The alkylation reaction is carried out in the presence of a non-nucleophilic base (e.g., cesium carbonate, sodium hydride, or potassium carbonate) and in a suitable polar aprotic organic solvent (e.g., ether, tetrahydrofuran, dioxane, dimethylformamide, and the like). The thioether is then oxidized to the sulfone with a suitable oxidizing agent such as m-chloroperoxybenzoic acid, sodium periodate, potassium hydrogen persulfate, sodium hypochlorite, and the like.

In method B, compound (I) where $R^3$ is —$SO_2NR^{13}R^{14}$ is prepared by reacting the 2-naphthalenesulfonyl chloride 3 with an excess amount of an amine of formula $NHR^{13}R^{14}$ in a suitable organic solvents (e.g., dioxane, tetrahydrofuran, and the like). Also, compound (I) where $R^{13}$ and/or $R^{14}$ are hydrogen can be alkylated/acylated to a corresponding compound of formula (I) where $R^{13}$ and/or $R^{14}$ are not hydrogen, if desired, by reacting it with a suitable alkylating or acylating agent, in the presence of a base (e.g., sodium carbonate, sodium hydride, triethylamine, and the like) and in a polar aprotic solvent such as methylene chloride, dioxane, and the like.

The preparation of a compound of formula (I) where A is —C(O)—, Z is 4-fluorophenyl, $R^1$ is —OMe, and $R^3$ is —$SO_2NH_2$ by this method is described in Example 1.

Scheme B describes the synthesis of a compound of formula (I) where A is —C(O)— and $R^3$ is —$SO_2R^{12}$ —$SO_2NR^{13}R^{14}$ from a 1-naphthoic acid 4 where $R^1$ is an ortho-para directing group.

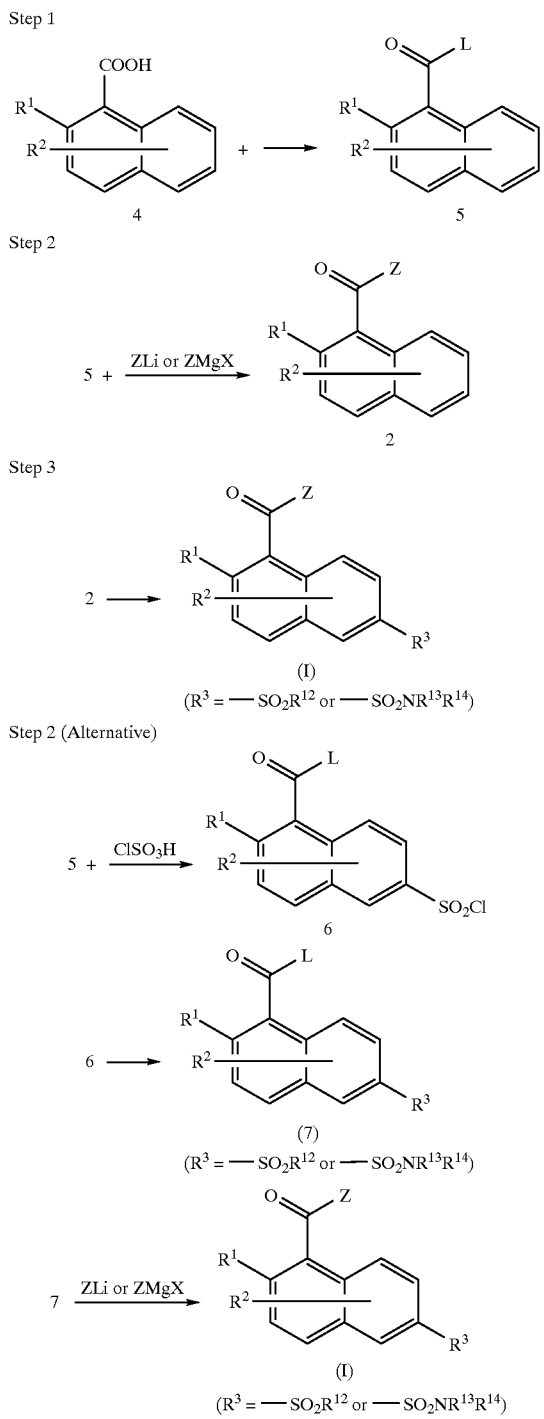

In Step 1, an acid derivative of formula 5 where L is a leaving group under organometallic displacement reaction conditions [e.g., alkoxy (preferably methoxy or ethoxy), dialkylamino, or preferably N,O-dimethylhydroxylamino] is prepared from a 1-naphthoic acid of formula 4 by 5 methods well known in the field of organic chemistry. For example, compound 5 where L is a N,O-dimethylhydroxylamino group can be prepared by first forming the acid chloride derivative of 4 with a suitable chlorinating agent such as oxalyl chloride, followed by treatment with N,O-dimethyl-hydroxylamine hydrochloride in the presence of an organic base such as triethylamine. Generally, the 1-naphthoic acids of formula 4 are commercially available.

In Step 2, a 1-aroylnaphthalene of formula 2 is prepared by reacting 5 with an organometallic reagent such as a Grignard reagent or an organolithium reagent (ZMgX or ZLi) under the reaction conditions such as those described in Takei, M., *Chem. Lett.*, 687 (1974) and Nahm, S., Weinreb, A. M., *Tet. Lett.*, 22, 3815, (1981).

In Step 3, compound 2 is converted to a compound of formula (I) where $R^3$ is —$SO_2R^{12}$ or —$SO_2NR^{13}R^{14}$ by proceeding as described in Scheme A, Steps 2 and 3.

Alternatively, compound (I) where $R^3$ is —$SO_2R^{12}$ or —$SO_2NR^{13}R^{14}$ is prepared as shown in Step 2 (alternative), by first preparing a 2-naphthalenesulfone or a 2-naphthalene-sulfonamide of formula 7 from the acid derivative 5, utilizing the reaction conditions described in Scheme A, Steps 2 and 3. Compound 7 is then converted to a corresponding compound of formula (I), by proceeding as described in Scheme B, Step 2 above.

Scheme C describes the synthesis of a compound of formula (I) where A is —C(O)— and $R^3$ is —$SO_2R^{12}$ or —$SO_2NR^{13}R^{14}$ from a naphthalenesulfonic acid 8 where $R^1$ is an ortho-para directing group.

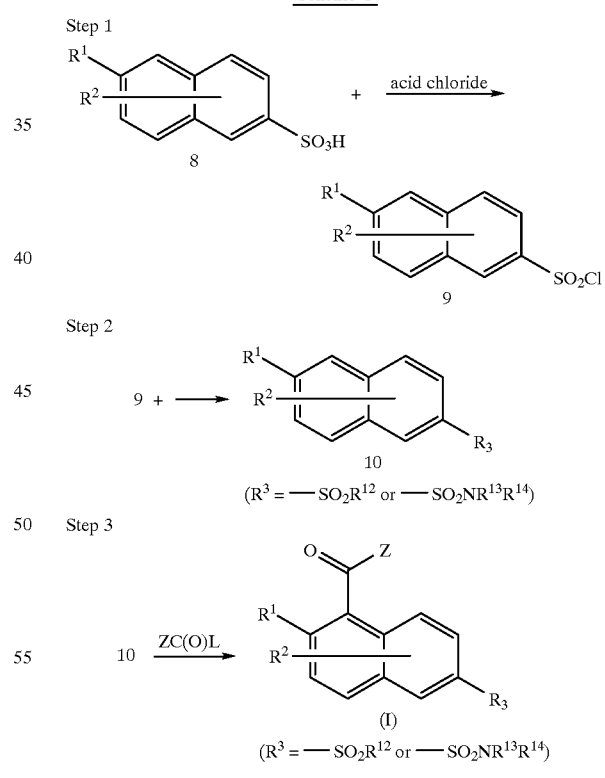

In Step 1, a 2-naphthalenesulfonyl chloride of formula 9 is prepared by reacting the 2-naphthalenesulfonic acid with an acid chloride such as thionyl chloride or oxalyl chloride.

In Step 2, a 2-naphthalenesulfone or a 2-naphthalenesulfonamide of formula 10 is prepared from compound 9 by proceeding as described in Scheme A, Step 3.

In Step 3, compound 10 is acylated at the 5-position to give a compound of formula (I) where $R^3$ —$SO_2R^{12}$ or —$SO_2NR^{13}R^{14}$ by proceeding as described in Scheme A, Step 1.

Scheme D describes the synthesis of compounds of formula (I) where A is —C(O)— and $R^3$ is —$SO_2R^{12}$ or —$SO_2NR^{13}R^{14}$ from bromonaphthalenes 11 where $R^1$ is an ortho-para directing group.

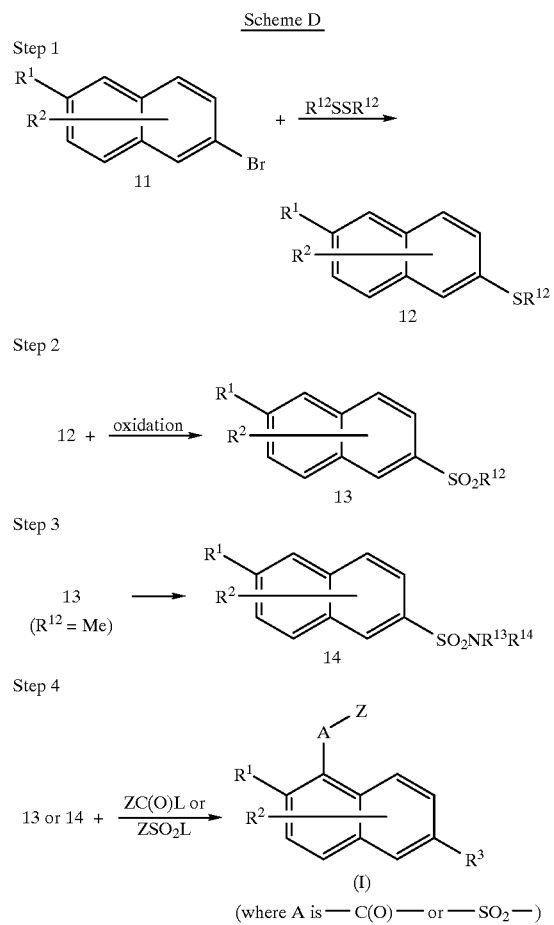

In Step 1, a naphthalene thioether of formula 12 is prepared by reacting a bromonaphthalene of formula 11 with a disulfide $R^{12}SSR^{12}$ or $R^{12}SO_2SR^{12}$ (where $R^{12}$ is as defined in the Summary of the invention) under an inert atmosphere. The nucleophilic substitution reaction can be carried out stepwise by first converting the bromonaphthalene to an organometallic reagent with a strong base such as n-butyllithium followed by treatment with the disulfide or it can be carried out directly in the presence of a copper catalyst such as copper powder, copper iodide, and the like. Suitable solvents for the reaction are polar aprotic solvents such as tetrahydrofuran, dimethylformamide, hexamethylphosphoramide, and the like.

In Step 2, the thioether 12 is oxidized to the naphthalenesulfone 13 by proceeding as described in Scheme A, Step 3, method A.

In Step 3, compound 13 (where $R^{12}$ is methyl) can optionally be converted to a corresponding sulfonamide where $R^{13}$ and $R^{14}$ are hydrogen by following the literature procedure described in Huang, H., et al, *Tet. Lett.*, 7201, (1995). This sulfonamide can be alkylated to give the corresponding mono- or di- N-alkylated derivatives by utilizing the reaction conditions described in Scheme A, Step 3, method B.

In Step 4, the naphthalenesulfone 13 or the sulfonamide 14 is acylated or sulfonylated at the 5-position (when $R^1$ is an ortho-para directing group) to give a compound of Formula (I) where A is —C(O)— or —$SO_2$— and $R^3$ is —$SO_2R^{12}$ or —$SO_2NR^{13}R^{14}$ by proceeding as described in Scheme A, Step 1.

The preparation of compounds of formula (I) where A is —C(O)— or —$SO_2$—, Z is 4-fluorophenyl, $R^1$ is OMe, and $R^3$ is —$SO_2Me$ by this method are described in Example 2 and 3.

The preparation of a compound of formula (I) where A is —C(O)—, Z is 4-fluorophenyl, $R^1$ is —CN, and $R^3$ is —$SO_2Me$ by this method is described in Example 6.

Scheme E describes the synthesis of compounds of formula (I) where A is a bond, —O—, —$NR^5$—, or —$S(O)_n$— where n is an integer from 0 to 2, $R^5$ is hydrogen or alkyl, and $R^3$ is —$SO_2R^{12}$ or —$SO_2NR^{13}R^{14}$ from 5-amino-2-naphthalenesulfonic acids 15.

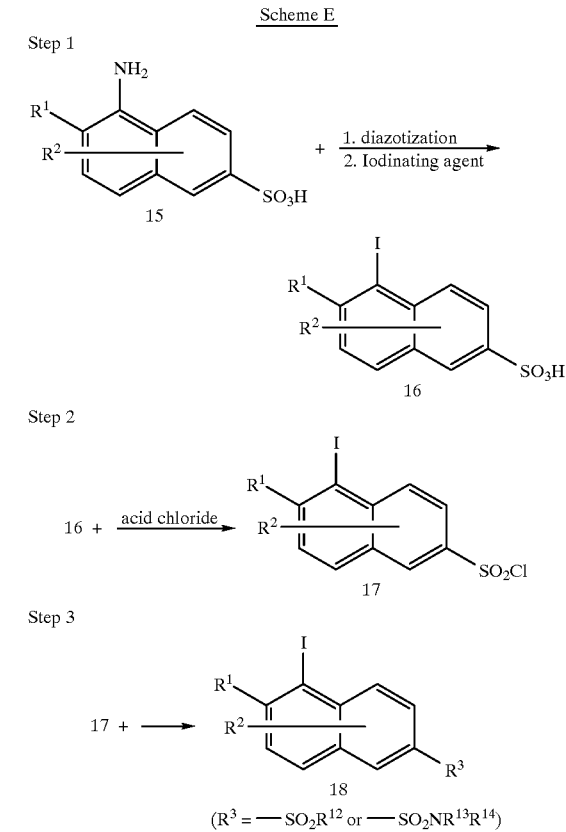

Step 4

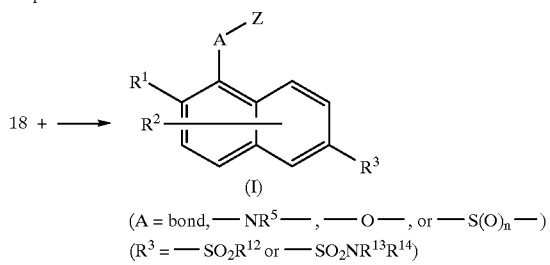

(A = bond, —NR⁵—, —O—, or —S(O)$_n$—)
(R³ = —SO$_2$R$^{12}$ or —SO$_2$NR$^{13}$R$^{14}$)

In Step 1, a 5-iodo-2-naphthalenesulfonic acid of formula 16 is prepared by converting a 5-amino-2-naphthalenesulfonic of formula 15 to a diazonium salt, which upon treatment with an iodinating reagent (e.g., I$_2$ or KI) gives the 5-iodo compound. This conversion can be carried out by utilizing the reaction conditions described in Heaney, H. and Millar. I. T., *Org. Synth.*, 40, 105, (1960). 5-Amino-2-naphthalenesulfonic acid is commercially available or can be prepared by nitration of the corresponding naphthalenesulfonic acid followed by reduction of the nitro group to an amine.

In Step 2, a 5-iodo-2-naphthalenesulfonyl chloride of formula 17 is prepared from the 5-iodo-2-naphthalenesulfonic acid 16 by utilizing the reaction conditions described in Scheme C, Step 1.

In Step 3, a 5-iodo-2-naphthalene of formula 18 where R³ is —SO$_2$R$^{12}$ or —SO$_2$NR$^{13}$R$^{14}$ are prepared from compound 17 by utilizing the reaction conditions described in Scheme A, Step 3, methods A or B respectively.

In Step 4, compounds of formula 18 are converted to compounds of formula (I) where A is a bond, —NR⁵— (where R⁵ is hydrogen or alkyl), —O—, or —S— by following published literature procedures. Where A is a bond, see, Stille, J. K., *Agnew. Chem. Intl. Ed.*, 25, 508, (1980), McKean, D. R., Parrinello, G., Renaldo, A. F., and Stille, S. K., *J. Org. Chem.*, 52,422, (1987) and Suzuki, *Syn. Commun.*, 11, 513, (1981). Where A is a —NR⁵— (where R⁵ is hydrogen or alkyl), —O— or —S—, see, Yamamoto, T., *Can. J. Chem.*, 61, 86, (1983); Burnell, J. F., *Chem. Rev.*, 49, 392, (1951); and Campbell, J. R., *J. Org. Chem.*, 29, 1830, (1964) and Tesafaferri, L., Tiecco, M., Tingol, M., Chianelli, D., and Menfanucci, M., *Synthesis.*, 751, (1983) respectively.

Additional Processes

Compounds of formula (I) can also be prepared by modification of a group present on a corresponding compound of formula (I). For example, a compound of formula (I) where R¹ is hydroxy, alkenyloxy, cycloalkyloxy, cycloalkylalkyloxy, haloalkyloxy, —OCONR⁹R$^{10}$ or —OSO$_2$R$^{11}$ may be prepared by de-alkylation of an alkoxy substituent on the corresponding compound of formula (I) followed by treatment with an appropriate alkylating, acylating or sulfonylating agents. The transformation can be carried out by methods well known in the field of organic chemistry. Compounds of formula (I) where R¹ is hydrogen, alkyl, alkenyl, cyano, halo, alkoxycarbonyl, —CONR⁹R$^{10}$ can be prepared from the corresponding compounds of formula (I) where R¹ is hydroxy by following literature procedures described in Ortar. G., *Tett. Lett.*, 27, 5541 (1986); Stille, J. K., *J. Org. Chem.*, 52, 422, (1987); and Capri, W., *J. Org. Chem.*, 55, 350, (1990).

Compounds of formula (I) where A is —CHOH—, —CH$_2$—, —C=NOR⁴— can be prepared from corresponding compounds of formula (1) where A is —C(O)—. These transformations can be carried out by reduction of the carbonyl group or by treatment with an appropriate hydroxy or alkoxyamine by methods well known in the field of organic chemistry.

The conversion of compounds of formula (I) where R¹ is methoxy and hydroxy to corresponding compounds of formula (I) where R¹ is hydroxy, cyano, and hydrogen respectively are described in Examples 4 and 5 respectively.

It will be recognized by one skilled in the art that these transformation are not limited to the R¹ position but may be carried out at other positions in the compound of formula (I).

General Utility

The compounds of the invention are inhibitors of prostaglandin G/H Synthase I and II (COX I and COX II), especially COX II, in vitro, and as such are expected to possess both anti-inflammatory and analgesic properties in vivo. See, for example, Goodman and Gilmans's "The Pharmacological Basis of Therapeutics", Ninth Edition, McGraw Hill, New York, 1996, Chapter 27. The compounds, and compositions containing them, are therefore useful as anti-inflammatory and analgesic agents in mammals, especially humans. They find utility in the treatment of fever, inflammation and pain caused by conditions such as rheumatic fever, symptoms associated with influenza or other viral infections, low back and neck pain, dysmenorrhoea, headache, toothache, sprains, myositis, synovitis, arthritis (rheumatoid arthritis and osteoarthritis), gout, ankylosing spondylitis, bursitis, bums or injuries. They maybe used to inhibit prostanoid-induced smooth muscle contractions (e.g., in the treatment of dysmenorrhoea, premature labor and asthma) and to treat autoimmune disorders (such as systemic lupus erythematosus and type I diabetes).

As inhibitors of prostaglandin G/H Synthase, the compounds of this invention are also expected to be useful in the prevention and treatment of cancer, in particular colon cancer. It has been shown that COX-2 gene expression is upregulated in human colorectal cancers and that drugs that inhibit prostaglandin G/H Synthase are effective in animal models of cancer (Eberhart, C. E., et. al., *Gastroenterology,* 107, 1183–1188, (1994), and Ara, G. and Teicher, B. A., *Prostaglandins, Leukotrienes and Essential Fatty Acids,* 54, 3–16, (1996)). In addition, there is epidemiological evidence that shows a correlation between use of drugs that inhibit prostaglandin G/H synthase and a reduced risk of developing colorectal cancer, (Heath, C. W. Jr., et. al., *Cancer,* 74, No. 10, 2885–8, (1994)).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients, (Rogers, J., et. al., *Neurology,* 43, 1609, (1993)). Also, the use of drugs which inhibit prostaglandin G/H synthase has been linked epidemiologically with a delayed onset of Alzheimer's disease, (Breitner, J. C. S., et. al., *Neurobiology of Aging,* 16, No. 4, 523, (1995) and Neurology, 44, 2073, (1994)).

Testing

The anti-inflammatory activity of the compounds of this invention may be assayed by measuring the ability of the compound to inhibit COX I and COX II, especially COX II, in vitro, using a radiometric assay, as described in more detail in Example 8. It may also be assayed by in vivo assays such as the Rat Carrageenan Paw and Rat Air-Pouch assays, as described in more detail in Examples 9 and 10. The analgesic activity of the compounds of this invention may be assayed by in vivo assays such as the Randall-Selitto assay and the rat arthritis pain model, as described in Example 11.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of formula (I) may range from approximately 0.005–10 mg per kilogram body weight of the recipient per day; preferably about 0.05–1 mg/kg/day. Thus, for administration to a 70 kg person, the dosage range would preferably be about 3.5 mg to 70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of formula (I) based on the total formulation, with the balance being one or more suitable pharmaceutical excipients. Preferably, the compound is present at a level of about 1–80 wt %. Representative pharmaceutical formulations containing a compound of formula (I) are described in Example 7.

EXAMPLES

The following preparations and examples are given to enable those skilled in the art to more clearly understand and to practice the present invention. They should not be considered as limiting the scope of the invention, but merely as being illustrative and representative thereof.

Abbreviations used in the examples are defined as follows: "HCl" for hydrochloric acid, "DMF" for dimethylformamide, "NaOH" for sodium hydroxide, and "DMSO" for dimethylsulfoxide.

Example 1

Synthesis of 5-(4-fluorobenzoyl)-6-methoxy-2-naphthalenesulfonamide [following Scheme A, Steps 1, 2 and 3 (method B)]

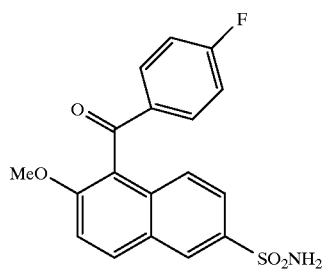

Step 1

A solution of 2-methoxynaphthalene (20.0 g, 120 mmol) and 4-fluorobenzoyl chloride (15 ml, 126 mmol) in methylene chloride (200 ml) was cooled in an ice bath under nitrogen and aluminum chloride (18.5 g, 129 mmol, 1.1 equiv.) was added portionwise over 10 minutes. The reaction mixture was stirred at room temperature for 3 h and then poured into 2N HCl (500 ml). The product was extracted into methylene chloride, and washed with brine, and dried over sodium sulfate. The organic layer was concentrated in vacuo to give 34.6 g of 1-(4-fluorobenzoyl)-2-methoxynaphthalene as a solid (97% yield) which was used in the next step without further purification.

Step 2

1-(4-fluorobenzoyl)-2-methoxynaphhthalene (4.0 g, 14.2 mmol), [prepared as described in step 1], was dissolved in chlorosulfonic acid (10 ml). After stirring at room temperature for 15 minutes, the reaction mixture was carefully poured into ice and the product was extracted into ethyl acetate. The organic layer was washed with brine, dried over sodium sulfate and concentrated in vacuo to give 5.39 g of 5-(4-fluorobenzoyl)-6-methoxy-2-naphthalenesulfonyl chloride which was used in the next step without further purification.

Step 3

A solution of 5-(4-fluorobenzoyl)-6-methoxy-2-naphthalenesulfonyl chloride (5.39 g, 14.2 mmol), [prepared as described in step 2 above], in dioxane (100 ml), was cooled in an ice bath under nitrogen, and concentrated ammonium hydroxide (20 ml) was added dropwise. After 1h, the dioxane was removed under reduced pressure and the residue was partitioned between water and ethyl acetate. The organic layer was separated and washed with brine, dried over sodium sulfate and concentrated in vacuo. The crude product was purified by flash chromatography (gradient elution, 20–60% ethyl acetate/hexane) and then recrystallized from ethyl acetate/hexane to afford 2.7 g of 5-(4-fluorobenzoyl)-6-methoxy-2-naphthalene-sulfonamide as white crystals.

Proceeding as described in Example 1 above, but substituting 4-fluorobenzoyl chloride in step 1, with: benzoyl chloride;
4-chlorobenzoyl chloride;
4-methylbenzoyl chloride;
2-fluorobenzoyl chloride;
3-fluorobenzoyl chloride; and
4-acetoxybenzoyl chloride (prepared from 4-acetoxybenzoic acid); gave, respectively,
5-benzoyl-6-methoxy-2-naphthalenesulfonamide;
5-(4-chlorobenzoyl)-6-methoxy-2-naphthalenesulfonamide;
5-(4-methylbenzoyl)-6-methoxy-2-naphthalenesulfonamide;
5-(2-fluorobenzoyl)-6-methoxy-2-naphthalenesulfonamide;
5-(3-fluorobenzoyl)-6-methoxy-2-naphthalenesulfonamide; and
5-(4-hydroxybenzoyl)-6-methoxy-2-naphthalenesulfonamide.

Example 2

Synthesis of 5-(4-fluorobenzoyl)-6-methoxy-2-methylsulfonylnaphthalene (following Scheme D)

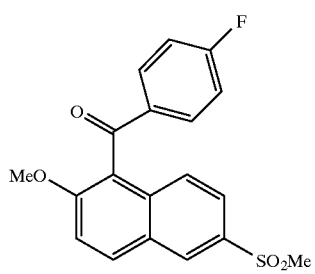

Step 1

A solution of 2-bromo-6-methoxynaphthalene (22.2 g, 93.6 mmol) in tetrahydrofuran (500 ml) was cooled to −78° C. and n-butyllithium (75 ml 1.6 M in THF, 121.7 mmol) was added dropwise over 15 minutes. After 0.5 h, dimethyl disulfide (13 ml, 140 mmol) was added and the reaction mixture was allowed to warm to room temperature. After 16 h, 1N sodium hydroxide (100 ml) was added and the reaction mixture was stirred for 1 h. The organic layer was separated and washed with 1N sodium hydroxide, 5% aqueous sodium sulfite, and brine, and dried over sodium sulfate. The solvent was removed in vacuo and the crude product was recrystallized form ethyl acetate and hexane to give 11.1 g of 2-methoxy-6-methylthio-naphthalene as a solid (58% yield).

Step 2

To a solution of 2-methoxy-6-methylthionaphthalene (1.0 g, 4.9 mmol), [prepared as described in Step 1], in methylene chloride (50 ml) was added 3-chloroperoxybenzoic acid (3.5 g, 10.3 mmol, 50–60%) portionwise. After 0.5 h, the reaction mixture was cooled in an ice bath, sodium sulfite ( 0.53 g, 4.2 mmol) was added and the stirring was continued for another 20 minutes. The reaction mixture was then poured in water and the organic layer was separated and dried over sodium sulfate. The solvent was removed in vacuo and the crude product was purified by flash chromatography (gradient elution 30–50% ethyl acetate/hexanes) to give 930 mg of 2-methoxy-6-methylsulfonylnaphthalene (80% yield).

Step 3

To a solution of 2-methoxy-6-methylsulfonylnaphthalene (0.93 g, 3.93 mmol), [prepared as described in step 2 above], in 1,2-dichloroethane (40 ml) was added 4-fluorobenzoyl chloride (0.93 ml, 7.87 mmol) and aluminum chloride (1.05 g, 7.87 mmol) and the reaction mixture was heated at reflux. After 16 h, the reaction mixture was poured in 2N HCl and extracted into methylene chloride. The organic layer was separated and washed with water and dried over sodium sulfate. The solvent was removed in vacuo and the crude product was purified by flash chromatography (gradient elution 10–60% ethyl acetate/ hexanes) to give 1.2 g of 5-(4-fluorobenzoyl)-6-hydroxy-2-methylsulfonyl-naphthalene as a tan solid (89% yield).

Step 4

A mixture of 5-(4-fluorobenzoyl)-6-hydroxy-2-methylsulfonylnaphthalene (1.0 g, 2.9 mmol), [prepared as described in step 3 above], methyl iodide (0.65 ml, 10.45 mmol), and potassium carbonate (0.64 g, 4.65 mmol) in N,N-dimethylformamide (10 ml) was stirred at room temperature. After 16 h, the reaction mixture was diluted with water and extracted into ethyl acetate. The organic layer was separated, washed with brine, and dried over sodium sulfate. The solvent was removed in vacuo and the crude product was purified by flash chromatography (gradient elution 40–100% ethyl acetate/hexanes) to give 1.0 g of 5-(4-fluorobenzoyl)-6-methoxy-2-methylsulfonylnaphthalene as a solid (96% yield).

Substituting 4-fluorobenzoyl chloride with benzoyl chloride in step 3 of this example, gave a mixture of 5-benzoyl-6-methoxy-2-methylsulfonylnaphthalene and 5-benzoyl-6-hydroxy-2-methylsulfonylnaphthalene which were separated by flash chromatography (gradient elution 20–50% ethyl acetate/hexanes).

Proceeding as described in Example 2 above, but substituting 4-fluorobenzoyl chloride with 4-chlorobenzoyl chloride in step 3, gave a mixture of 5-(4-chlorobenzoyl)-6-methoxy-2-methylsulfonylnaphthalene and 5-(4-chlorobenzoyl)-6-hydroxy-2-methylsulfonylnaphthalene which were separated by flash chromatography.

Proceeding as described in Example 2 above, but substituting 4-fluorobenzoyl chloride with 2-fluorobenzoyl chloride in step 3, gave a mixture of 5-(2-fluorobenzoyl)-6-methoxy-2-methylsulfonylnaphthalene and 5-(2-fluorobenzoyl)-6-hydroxy-2-methylsulfonylnaphthalene which were separated by flash chromatography.

Example 3

Synthesis of 5-(4-fluorophenylsulfonyl)-6-methoxy-2-methylsulfonylnaphthalene (following Scheme D)

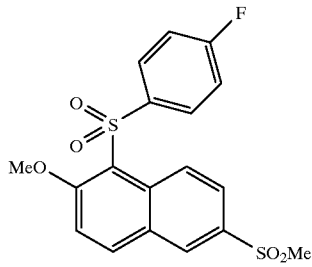

Aluminum chloride (1.13 g, 8.46 mmol) was added to a solution of 2-methoxy-6-methylsulfonylnaphthalene (1.0 g, 4.2 mmol) [prepared as described in example 2 above], and 4-fluorobenzenesulfonyl chloride (1.65 g, 8.46 mmol) in 1,2 dichloroethane (40 ml). The reaction mixture was heated at reflux for 16 h, and then poured into 2N HCl and extracted into methylene chloride. The organic layer was separated, washed with water and brine, and dried over sodium sulfate. Purification by flash chromatography gave 0.1 g of 5-(4-fluoro-phenylsulfonyl)-6-methoxy-2-methylsulfonylnaphthalene as a solid (16% yield).

Example 4

Synthesis of 5-(4-fluorobenzoyl)-6-cyano-2-naphthalenesulfonamide

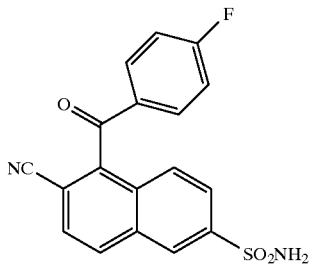

Step 1

Boron tribromide (55.7 ml, 1M solution in methylene chloride) was added to a suspension of 5-(4-fluorobenzoyl)-6-methoxy-2-naphthalenesulfonamide (5 g, 14 mmol), [prepared as described in example 1], in methylene chloride (100 ml) at 0° C. After 30 minutes, the reaction mixture was poured into brine and the product was extracted into methylene chloride. The organic layer was washed with brine, dried over sodium sulfate, and concentrated to dryness in vacuo. The crude product was purified by chromatography (silica gel, gradient elution, 20–80% ethyl acetate/hexane) to afford 4.0 g of 5-(4-fluorobenzoyl)-6-hydroxy-2-naphthalenesulfonamide as a solid (83% yield).

Step 2

Pyridine (4.25 ml, 52.1 mmol) and trifluoromethanesulfonic anhydride (4.4 ml, 26.1 mmol) were added to a solution of 5-(4-fluorobenzoyl)-6-hydroxy-2-naphthalenesulfonamide (3.0 g, 8.7 mmol), [prepared as described in step 1 above], in methylene chloride (50 ml) at 0° C. After 0.5 h, 1N sodium bisulfate was added and the stirring was continued for an additional 30 minutes. The organic layer was separated, washed with brine, and dried over sodium sulfate. The solvent was removed in vacuo to give 3.1 g of 5-(4-fluorobenzoyl)-6-trifluoromethylsulfonyloxy-2-naphthalenesulfonamide as an oil (75% yield).

Step 3

A mixture of 5-(4-fluorobenzoyl)-6-trifluoromethylsulfonyloxy-2-naphthalenesulfonamide (1.0 g, 2.1 mmol) [prepared as described in step 2 above,], potassium cyanide (0.15 mg, 2.3 mmol), and tetrakis(triphenylphosphine) palladium(0) in dioxane (15 ml) was heated at reflux under argon. After 2 h, the reaction mixture was cooled to RT, poured into brine, and the product was extracted into ethyl acetate. The organic layer was dried with sodium sulfate and concentrated in vacuo. The crude product was purified by flash chromatography (gradient elution, 20–50% ethyl acetate /hexane) and then recrystallized from ethyl acetate-hexane to give 0.44 g of 5-(4-fluorobenzoyl)-6-cyano-2-naphthalenesulfonamide as a white solid (54% yield).

Proceeding as described in Example 4 above, but substituting 5-(4-fluorobenzoyl)-6-methoxy-2-naphthalenesulfonamide with 5-(2-fluorobenzoyl)-6-methoxy-2-naphthalenesulfonamide gave 5-(2-fluorobenzoyl)-6-cyano-2-naphthalenesulfonamide.

Example 5

Synthesis of 5-(4-fluorobenzoyl)-2-methylsulfonylnaphthalene

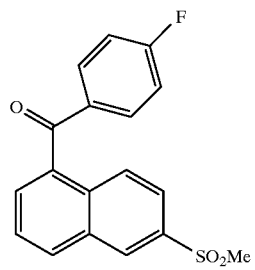

Step 1

Pyridine (0.74 ml, 9.2 mmol) and trifluoromethanesulfonic anhydride (0.78 ml, 4.6 mmol) were added to a solution of 5-(4-fluorobenzoyl)-6-hydroxy-2-methylsulfonylnaphthalene (0.4 g, 1.2 mmol), [prepared as described in example 2 above], in methylene chloride at 0° C. After 0.5 h, 1N sodium bisulfate was added and the stirring was continued for an additional 30 minutes. The organic layer was separated, washed with brine, and dried over sodium sulfate. The solvent was removed in vacuo to give 0.62 g of 5-(4-fluorobenzoyl)-6-trifluoromethylsulfonyloxy-2-methylsulfonylnaphthalene as an oil.

Step 2

A mixture of 5-(4-fluorobenzoyl)-6-trifluoromethylsulfonyloxy-2-methylsulfonylnaphthalene (0.3 g, 0.63 mmol), [prepared as described in step 1 above], formic acid (0.096 ml, 2.5 mmol), triethylamine(0.36 ml, 2.5 mmol), palladium acetate (14 mg, 0.06 mmol), and 1,3-bis(diphenylphosphino)propane (0.10 g, 0.03 mmol) in DMF (10 ml) was stirred at room temperature. After 16 h, the reaction mixture was poured into brine and extracted into ethyl acetate. The organic layer was separated, dried over sodium sulfate, and concentrated in vacuo. The crude product was purified by flash chromatography (gradient elution 10–30% ethyl acetate/hexanes) and then recrystallized from ethyl acetate -hexanes to give 0.1 g of 5-(4-fluoro-benzoyl)-2-methylsulfonylnaphthalene as a solid (48% yield).

Example 6

Synthesis of 5-(4-fluorobenzoyl)-6-cyano-2-methylsulfonylnaphthalene

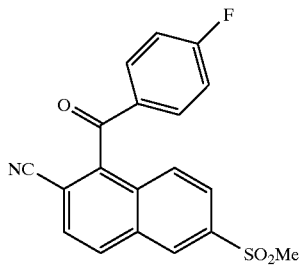

Step 1

Pyridine (0.38 ml, 4.65 mmol) and trifluoromethanesulfonic anhydride (0.39 ml, 2.32 mmol) were added to a solution of 5-(4-fluorobenzoyl)-6-hydroxy-2-methylsulfonylnaphthalene (0.4 g, 1.16 mmol), [prepared as described in Example 2, step 3 above], in methylene chloride (10 ml) at 0° C. After 0.5 h, additional amounts of pyridine (0.38 ml, 4.65 mmol) and trifluoromethanesulfonic anhydride (0.39 ml, 2.32 mmol) were added and stirring was continued. After 0.5 h, 1N sodium bisulfate was added and the stirring was continued for an additional 30 minutes. The organic layer was separated, washed with brine, and dried over sodium sulfate. The solvent was removed in vacuo to give 0.6 g of 5-(4-fluorobenzoyl)-6-trifluoromethylsulfonyloxy-2-methylsulfonylnaphthalene as an oil (90% yield).

Step 2

A mixture of 5-(4-fluorobenzoyl)-6-trifluoromethylsulfonyloxy-2-methylsulfonylnaphthalene (2.5 g, 5.2 mmol) [prepared as described in step 1 above,], potassium cyanide (0.41 g, 6.3 mmol), and tetrakis(triphenylphosphine)palladium(0) (0.30 g, 0.26 mmol) in dioxane (50 ml) was heated at reflux under argon. After 16 h, the reaction mixture was cooled to RT, poured into brine, and the product was extracted into ethyl acetate. The organic layer was dried with sodium sulfate and concentrated in vacuo. The crude product was purified by flash chromatography (gradient elution, 10–60% ethyl acetate /hexane) and then recrystallized from ethyl acetate-hexane to give 1.16 g of 5-(4-fluorobenzoyl)-6-cyano-2-methylsulfonylnaphthalene as a solid (63% yield).

Proceeding as described in Example 6 above, but substituting 5-(4-fluorobenzoyl)-6-hydroxy-2-methylsulfonylnaphthalene with:

5-benzoyl-6-hydroxy-2-methylsulfonylnaphthalene;

5-(4-chlorobenzoyl)-6-hydroxy-2-methylsulfonylnaphthalene; and 5-(2-fluorobenzoyl)-6-hydroxy-2-methylsulfonylnaphthalene, gave 5-benzoyl-6-cyano-2-methylsulfonylnaphthalene;

5-(4-chlorobenzoyl)-6-cyano-2-methylsulfonylnaphthalene; and 5-(2-fluorobenzoyl)-6-cyano-2-methylsulfonylnaphthalene, respectively.

Proceeding as described in Example 6 above, but substituting potassium cyanide with trimethylaluminum in step 2, gave 5-(4-fluorobenzoyl)-6-methyl-2-methylsulfonylnaphthalene.

Example 7

The following are representative pharmaceutical formulations containing a compound of formula (I).

Tablet formulation

The following ingredients are mixed intimately and pressed into single scored tablets.

| Ingredient | Quantity per tablet, mg |
|---|---|
| compound of this invention | 400 |
| corn starch | 50 |
| croscarmellose sodium | 25 |
| lactose | 120 |
| magnesium stearate | 5 |

Capsule formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s.to 100 ml |

Injectable formulation

The following ingredients are mixed to form an injectable formulation.

| Ingredient | Amount |
|---|---|
| compound of this invention | 0.4 mg |
| sodium acetate buffer solution, 0.4 M | 2.0 ml |
| HCl (1N) or NaOH (1N) | q.s. to suitable pH |
| water (distilled, sterile) | q.s. to 20 ml |

Example 8

Inhibition of COX I and COX II in vitro

The COX I and COX II inhibitory activity of compounds of this invention in vitro was determined using partially purified COX I and COX II enzymes, prepared as described in J. Barnett et. al., *Biochim. Biophys. Acta,* 1209, 130–139 (1994).

COX I and COX II samples were diluted with Tris-HCl buffer (SOmM Tris-HCl, pH 7.9) containing 2 mM EDTA and 10% glycerol and reconstituted by incubating first with 2 mM phenol for 5 minutes and then with 1 micromolar hematin for an additional 5 minutes. 125 μl of the reconstituted COX I or COX II enzyme were preincubated for 10 minutes at room temperature in a shaking water bath with the compounds of the invention dissolved in 2–15 μl of DMSO or the carrier vehicles (control samples). The enzyme reaction was initiated by adding 25 μl of 1-[14 C]arachidonic acid (80,000–100,000 cpm/tube; 20 micromolar final concentration) and the reaction was allowed to continue for an additional 45 seconds. The reaction was terminated by adding 100 μl of 2N HCl and 750 μl water. An aliquot (950 μl) of the reaction mixture was loaded onto a 1 ml $C_{18}$ Sep-Pak column (J. T. Baker, Phillipsburg, N.J.) which had been previously washed with 2–3 ml methanol and equilibrated with 5–6 ml distilled water. Oxygenated products were quantitatively eluted with 3 ml of acetonitrile/water/acetic acid (50:50:0.1, v/v) and the radioactivity in the eluate determined in a scintillation counter.

Compounds of this invention were active in this assay.

The COX inhibitory activities (expressed as $IC_{50}$, the concentration causing 50% inhibition of the COX enzyme being assayed) of some compounds of the invention and indomethacin as a comparator, were:

| CPD # | COX I $IC_{50}$, μM | COX II $IC_{50}$, μM |
|---|---|---|
| 1 | 20 | 0.51 |
| 4 | 2.8 | 0.84 |
| 5 | 0.46 | 0.56 |
| 14 | 47.7 | 0.076 |
| 15 | 62.5 | 0.68 |
| 20 | 6.0 | 0.45 |
| 42 | 40.9 | 2.0 |
| 64 | 0.9 | 0.7 |
| 65 | 300 | 0.7 |
| 66 | 100 | 0.3 |
| 91 | 90.8 | 0.92 |
| 92 | 646 | 5.9 |
| 93 | 435.6 | 7.84 |
| 94 | 805 | 2.43 |
| 95 | 1000 | 2.73 |
| 96 | >100 | 0.80 |
| 97 | >100 | 0.80 |
| 99 | >100 | 0.5 |
| 100 | >100 | 0.25 |
| 103 | 97 | 1.5 |
| 104 | 93 | 0.57 |
| Indomethacin | 0.4 | 14 |

Example 9

Anti-inflammatory activity

The anti-inflammatory activity of compounds of this invention was determined by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol. Med. 111, 544–547, (1962). This assay has been used as a primary in vivo screen for anti-inflammatory activity of most NSAIDs, and is considered predictive of human efficacy. Briefly, test materials were administered orally to female rats in a volume of 1 ml prepared as solutions or suspensions in an aqueous vehicle containing 0.9% sodium chloride, 0.5% sodium carboxymethyl-cellulose, 0.4% polysorbate 80, 0.9% benzyl alcohol and 97.3% distilled water. Control rats received vehicle alone. After 1 h 0.05 ml of a 0.5% solution of Carrageenan (Type IV Lambda, Sigma Chemical Co.) in 0.9% saline was injected into the subplantar region of the right hind paw. Three hours later the rats were euthanized in a carbon dioxide atmosphere; hind paws were removed by severing at the tatso-crural joint; and the left and right paws were weighed. The increase in weight of the right paw over the left paw was obtained for each animal and the mean increases were calculated for each group. The anti-inflammatory activity of the test materials is expressed as the percent inhibition of the increase in hind paw weight of the test group relative to the vehicle dosed control group.

Compounds of this invention were active in this assay.

The anti-inflammatory activities (expressed as % inhibition) of some of the compounds of the invention were:

| CPD # | Dose mg/Kg | % Inhibition |
|---|---|---|
| 1 | 10 | 29.94 |
| 4 | 10 | 26.41 |
| 5 | 30 | 27.49 |
| 17 | 30 | 19.56 |
| 20 | 30 | 33.85 |
| 64 | 6 | 30 |
| 65 | 12 | 30 |
| 66 | 12 | 30 |
| 91 | 10 | 29.48 |
| 92 | 30 | 19.88 |
| 93 | 30 | 6.25 |
| 95 | 30 | 15.5 |
| 96 | 30 | 38 |
| 97 | 30 | 40 |
| 99 | 10 | 38 |
| 104 | 30 | 33 |

Example 10

Inhibition of eicosanoid synthesis in vivo

The activity of compounds of this invention in inhibiting in vivo eicosanoid (prostaglandin $E_2$) synthesis in inflamed tissues was determined by the carrageenan-induced inflammation (air-pouch model) in rats, using a modification of the method described in Futaki, M., et al., "Selective Inhibition of NS-398 on prostanoid production in inflamed tissue in rat Carrageenan Air-pouch Inflammation"J. Pharm. Pharmacol. 45, 753–755, (1993) and Masferrer, J. L., et al.; "Selective Inhibition of inducible cyclooxygenase 2 in vivo is Antiflammatory and Nonulcerogenic" Proc. Natl. Acad. Sci. USA. 91, 3228–3232, (1994). In this assay, an air-pouch is created in the rat and the $PGE_2$ levels in the air-pouch exudate are measured by enzyme immunoassay. Briefly, male rats were anesthetized using a 60:40 $CO_2:O_2$ mixture and subsequently injected subcutaneously with 20 ml of sterilized air, under aseptic conditions, in the proximal area of the dorsum. This injection of sterile air causes the creation of a subcutaneous "air pouch". The next day, a further 10 ml of sterile air was injected into the previously formed pouch using the same technique. The test materials were administered orally in a volume of 1 ml/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats received vehicle alone. After 30 minutes, 5 ml of a 0.5% solution of carrageenan (Sigma, Lambda Type IV) was injected into the air pouch. The rats were euthanized 3 or 6 h after the compound administration. 10 ml of a solution containing 10 gg/l of indomethacin and 5.4 mM EDTA in 0.9% sterile saline was injected into the air pouch; the air pouch was cut open; and the exudate was harvested. The total exudate volume was recorded, and the samples were analyzed for $PGE_2$ and 6-keto $PGF_1$ by ELISA (Titerzyme®, PerSeptive Diagnostics, Boston, Mass.) and $TxB_2$ by radioimmuno assay (New England Nuclear Research, Boston, Mass., Catalog No. NEK-037), according to the manufacturer's directions.

The mean concentrations of $PGE_2$ were calculated for each group. The anti-inflammatory activity of test materials is expressed as the percent inhibition of $PGE_2$ formation in the test group relative to the control group.

Compounds of this invention were active in this assay.

The inflammatory activities (expressed as % inhibition of air pouch $PGE_2$ formation) of the compounds of this invention and indomethacin as a comparator were:

| CPD # | Dose mg/Kg | % Inhibition |
|---|---|---|
| 1 | 10 | 92 |
| 4 | 10 | 74.6 |
| 14 | 10 | 58.8 |
| 20 | 10 | 100 |
| 23 | 10 | 70.7 |
| 64 | 0.5 | 50 |
| 65 | 2 | 50 |
| 66 | 1 | 50 |
| 91 | 30 | 58.1 |
| 94 | 10 | 17.6 |
| 96 | 1 | 90 |
| 97 | 3 | 90 |
| 99 | 3 | 86 |
| 100 | 3 | 63 |
| 104 | 1 | 76.5 |
| Indomethacin | 2–5 | >70% |

Example 11

Analgesic Activity

The analgesic activity of the compounds of this invention may be determined by using a modification of the method described in Randall, L. O., and Selitto, J. J., "A Method for Measurement of Analgesic Activity on Inflamed Tissue", Arch. Int. Pharmacodyn., CXI, 4, 409, (1975) and Gans, et. al., "Anti-Inflammatory and Safety Profile of DuP 697, a Novel Orally Effective Prostaglandin Synthesis Inhibitor", J. Pharmacol. Exp. Ther., 254, No. 1, 180, (1990). In this assay, the male Sprague Dawley rats were injected with 0.1 ml of 20% brewer's yeast in deionized water (Sigma, St. Louis) in the subplantar region of the left hind foot. After 2 h, the test materials were administered orally in a volume of 1 ml/100 g body weight as solutions or suspensions in an aqueous vehicle containing 0.9% sodium chloride, 0.5% sodium carboxymethyl-cellulose, 0.4% polysorbate 80,0.9% benzyl alcohol and 97.3% water. Control rats received vehicle alone. After 1 h, the hindpaw was placed on the platform of a Basile Analgesy-Meter (Ugo Biological Research Apparatus, Italy, Model #7200) and mechanical force was applied to the dorsum of the rat's hindpaw. Compounds of the invention were active in this assay.

The analgesic activity of compounds of this invention may also be determined by using an adjuvant-induced arthritis pain model in the rat, where pain is assessed by the animal's vocal response to the squeezing or flexing of an inflamed ankle joint, as described in Winter C. A. and Nuss, G. W., "Treatment of Adjuvant Arthritis in rats with Anti-inflammatory Drugs", Arthritis Rheum., 9, 394–403, (1966) and Winter, C. A., Kling P. J., Tocco, D. J., and Tanabe, K., "Analgesic activity of Diflunisal [MK-647; 5-(2,4-Difluorophenyl)salicylic acid] in Rats with Hyperalgesia Induced by Freund's Adjuvant", J. Pharmacol. Exp. Ther., 211, 678–685, (1979).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound selected from the group of compounds represented by formula (I):

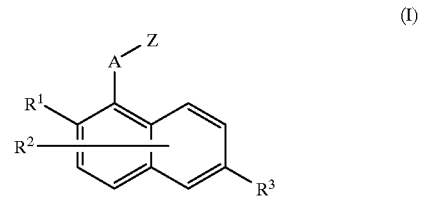

wherein:

A is a bond, —$CH_2$—, —CH(OH)—, —C=$NOR^4$—, —C(O)—, —$NR^5$—, —O—, or —S(O)$_n$— where n is an integer from 0 to 2, $R^4$ is hydrogen or alkyl, and $R^5$ is hydrogen, alkyl, or acyl;

Z is a group represented by formula (B), or (E):

where:
$n^1$ is 0 to 3;
X is O or S;
$R^6$ and $R^7$ are independently selected from hydrogen, alkyl, haloalkyl, cycloalkyl, cycloalkylalkyl, acyl, alkylthio, cycloalkylthio, cycloalkylalkylthio, alkoxy, cycloalkyloxy, cycloalkylalkyloxy, haloalkyloxy, alkenyl, halo, cyano, nitro, hydroxy, or —$NR^9R^{10}$ where $R^9$ and $R^{10}$ are independently hydrogen, alkyl, or acyl; or $R^6$ and $R^7$ when they are adjacent to each other form methylenedioxy or ethylenedioxy; $R^8$ is hydrogen, alkyl, haloalkyl, alkoxy, cycloalkyloxy, haloalkyloxy, alkylthio, cycloalkylthio, nitro, cyano, hydroxy, or halo;

$R^1$ is hydrogen, alkyl, alkenyl, alkynyl, haloalkyl, cycloalkyl, cycloalkylalkyl, alkoxy, alkenyloxy, cycloalkyloxy, cycloalkylalkyloxy, haloalkyloxy, hydroxyalkyloxy, alkoxyalkyloxy, alkylthio, cycloalkylthio, cycloalkylalkylthio, hydroxy, halo, cyano, carboxy, alkoxycarbonyl, acyl, —C=$NOR^4$, —$NR^9R^{10}$, —$CONR^9R^{10}$, —$OCONR^9R^{10}$, or —$OSO_2R^{11}$ where $R^4$, $R^9$, and $R^{10}$ are as previously defined and $R^{11}$ is alkyl, cycloalkyl, or haloalkyl;

$R^2$ is hydrogen, alkyl, alkoxy, halo, nitro, or —$NR^9R^{10}$; and $R^3$ is —$SO_2R^{12}$ or —$SO_2NR^{13}R^{14}$ where:
   $R^{12}$ is alkyl, hydroxyalkyl, alkoxyalkyl, carboxyalkyl, or alkoxycarbonylalkyl;
   $R^{13}$ is hydrogen, alkyl, or acyl; and
   $R^{14}$ is hydrogen, alkyl, haloalkyl, cycloalkyl, cycloalkylalkyl, alkenyl, hydroxyalkyl, alkoxyalkyl, alkoxycarbonylalkyl, amino, aminoalkyl, aryl, aralkyl, heteroaralkyl, heterocyclo, heterocycloalkyl, acyl, hydroxy, or alkoxy; or $R^{13}$ and $R^{14}$ together with the nitrogen atom to which they are attached optionally form a heterocycloamino group; and their pharmaceutically acceptable salts, prodrugs, individual isomers, and mixtures of isomers.

2. The compound of claim 1, wherein A is —C=NOR$^4$—.

3. The compound of claim 2, wherein Z is a group represented by formula (B) or (E).

4. The compound of claim 1, wherein A is —O—, —S— or —NR$^5$—.

5. The compound of claim 4, wherein Z is a group represented by formula (B) or (E).

6. The compound of claim 1, wherein A is —C(O)—.

7. The compound of claim 6, wherein R is —SO$_2$R$^{12}$.

8. The compound of claim 7, wherein:
   Z is a group represented by formula (B);
   $R^2$ is hydrogen; and
   $R^6$ and $R^7$ are independently selected from hydrogen, alkyl, cycloalkyl, alkoxy, ethenyl, halo, or —NR$^9$R$^{10}$ where $R^9$ and $R^{10}$ are alkyl.

9. The compound of claim 8, wherein $R^3$ is —SO$_2$-(alkyl).

10. The compound of claim 9, wherein:
   $R^1$ is hydrogen, alkyl, alkoxy, cycloalkoxy, 2-hydroxyethyloxy, hydroxy, halo, or cyano; and
   $R^6$ and $R^7$ are independently hydrogen, alkyl, alkoxy, or halo.

11. The compound of claim 10, wherein:
   $R^1$ is hydrogen, methyl, hydroxy, methoxy, chloro, or cyano; and
   $R^3$ is —SO$_2$Me.

12. The compound of claim 11, wherein $R^6$ and $R^7$ are independently selected from hydrogen, methyl, methoxy, fluoro, or chloro.

13. The compound of claim 12, wherein $R^6$ is at the 2-position and $R^7$ is at the 4-position.

14. The compound of claim 12, wherein $R^6$ is at the 3-position and $R^7$ is at the 4-position.

15. The compound of claim 13, wherein $R^1$ is cyano, and $R^6$ and $R^7$ are hydrogen namely, 5-benzoyl-6-cyano-2-methylsulfonylnaphthalene.

16. The compound of claim 13, wherein $R^1$ is cyano, $R^6$ is hydrogen, and $R^7$ is fluoro namely, 5-(4-fluorobenzoyl)-6-cyano-2-methylsulfonylnaphthalene.

17. The compound of claim 6, wherein $R^3$ is —SO$_2$NR$^{13}$R$^{14}$.

18. The compound of claim 17, wherein:
   Z is a group represented by formula (B);
   $R^2$ is hydrogen; and
   $R^6$ and $R^7$ are independently selected from hydrogen, alkyl, cycloalkyl, alkoxy, ethenyl, halo, or —NR$^9$R$^{10}$ where $R^9$ and $R^{10}$ are alkyl.

19. The compound of claim 18, wherein $R^3$ is —SO$_2$NHR$^{14}$ where $R^{14}$ is hydrogen, alkyl, hydroxy, or 2-hydroxyethyl.

20. The compound of claim 19, wherein:
   $R^1$ is hydrogen, alkyl, alkoxy, cycloalkoxy, 2-hydroxyethyloxy, hydroxy, halo, or cyano; and
   $R^6$ and $R^7$ are independently hydrogen, alkyl, alkoxy, or halo.

21. The compound of claim 20, wherein:
   $R^1$ is hydrogen, methyl, hydroxy, methoxy, chloro, or cyano; and
   $R^3$ is —SO$_2$NH$_2$.

22. The compound of claim 21, wherein $R^6$ and $R^7$ are independently hydrogen, methyl, methoxy, fluoro, or chloro.

23. The compound of claim 22, wherein $R^6$ is at the 2-position and $R^7$ is at the 4-position.

24. The compound of claim 22, wherein $R^6$ is at the 3-position and $R^7$ is at the 4-position.

25. The compound of claim 23, wherein $R^1$ is methoxy, $R^6$ is hydrogen, and $R^7$ is fluoro namely, 5-(4-fluorobenzoyl)-6-methoxy-2-naphthalenesulfonamide.

26. The compound of claim 23, wherein $R^1$ is cyano, $R^6$ is hydrogen, and $R^7$ is fluoro namely, 5-(4-fluorobenzoyl)-6-cyano-2-naphthalenesulfonamide.

27. The compound of claim 24, wherein $R^1$ is methoxy, $R^6$ is fluoro, and $R^7$ is hydrogen namely, 5-(3-fluorobenzoyl)-6-methoxy-2-naphthalenesulfonamide.

28. A pharmaceutical composition comprising a therapeutically effective amount of a compound of claim 1 and a pharmaceutically acceptable excipient.

29. A process for preparing a compound selected from the group of compounds of claim 1, which comprises:
   (1) reacting a compound of formula where $R^1$, $R^2$ and $R^{12}$ are as defined above, with an acylating agent of formula ZC(O)L where L is a leaving group under acylating conditions and Z is as defined above; and
   (2) optionally modifying any of the $R^1$, $R^2$, $R^6$, $R^7$, $R^8$ and $R^{12}$ groups.

30. The process of claim 29, wherein the compound of formula (I) is 5-(4-fluorobenzoyl)-6-cyano-2-methylsulfonylnaphthalene.

31. The process of claim 29, wherein the compound of formula (I) is 5-benzoyl-6-cyano-2-methylsulfonylnaphthalene.

32. A method of treatment of an inflammatory disease in a mammal treatable by administration of a prostaglandin G/H synthase inhibitor, comprising administration to the mammal a therapeutically effective amount of a compound of claim 1.

33. The method of claim 32, wherein the inflammatory disease is selected from myositis, synovitis, arthritis (rheumatoid arthritis and osteoarthritis), gout, ankylosing spondylitis and bursitis.

* * * * *

UNITED STATES PATENT AND TRADEMARK OFFICE
CERTIFICATE OF CORRECTION

PATENT NO. : 5,962,531
DATED : October 5, 1999
INVENTOR(S) : Rotstein et al.

It is certified that error appears in the above-identified patent and that said Letters Patent is hereby corrected as shown below:

Column 34, claim 1,
Line 41, after "Z is a group represented by formula (B), or (E):" add structures (B) and (E) as follows

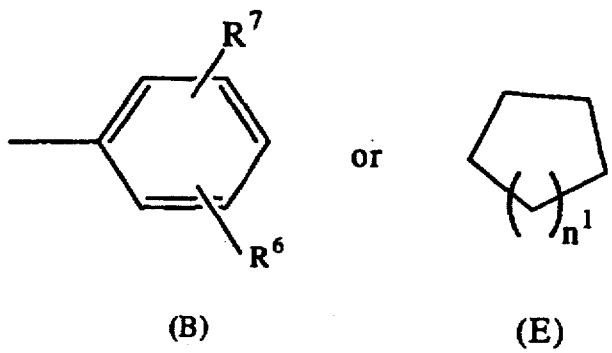

(B)  (E)

Lines 54-56, delete "$R^8$ is hydrogen, alkyl, haloalkyl, alkoxy, cycloalkyloxy, haloalkyloxy, alkythio, cycloalkylthio, nitro, cyano, hydroxy, or halo;"

Column 35, claim 1,
Line 11, delete the word "optionally"

Signed and Sealed this

Twenty-ninth Day of January, 2002

Attest:

*Attesting Officer*

JAMES E. ROGAN
*Director of the United States Patent and Trademark Office*